(12) United States Patent
Tucker

(10) Patent No.: US 6,916,817 B1
(45) Date of Patent: Jul. 12, 2005

(54) INHIBITORS OF METALLOPROTEINASES

(75) Inventor: Howard Tucker, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 131 days.

(21) Appl. No.: 09/980,593

(22) PCT Filed: May 31, 2000

(86) PCT No.: PCT/GB00/02085

§ 371 (c)(1),
(2), (4) Date: Dec. 4, 2001

(87) PCT Pub. No.: WO00/75108

PCT Pub. Date: Dec. 14, 2000

(30) Foreign Application Priority Data

Jun. 4, 1999 (EP) .............................................. 99401350

(51) Int. Cl.$^7$ .................... C07D 401/04; C07D 401/06; A61K 31/496; A61P 19/02; A61P 35/04
(52) U.S. Cl. .................. 514/253.01; 544/364; 544/360; 514/253.11; 514/253.13
(58) Field of Search ..................... 544/364; 514/253.01, 514/253.11, 253.13

(56) References Cited

U.S. PATENT DOCUMENTS 5,817,822 A    10/1998    MacPherson et al. ....... 546/194

FOREIGN PATENT DOCUMENTS

| DE | 198 02 350 | 7/1998 |
|---|---|---|
| WO | WO 99/02510 | 1/1999 |
| WO | WO 99/18074 | 4/1999 |
| WO | WO 99/38843 | 8/1999 |
| WO | WO 00/12478 | 3/2000 |

OTHER PUBLICATIONS

Coussens et al. {SCIENCE, vol. 295, Mar. 29, 2002}.*

* cited by examiner

*Primary Examiner*—Mark L. Berch
*Assistant Examiner*—Kahsay Habte
(74) *Attorney, Agent, or Firm*—Pillsbury Winthrop LLP

(57) ABSTRACT

Arylpiperazines of Formula I useful as metalloproteinase inhibitors, especially as MMP13 inhibitors.

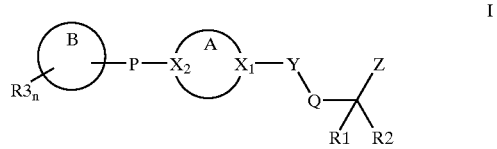

6 Claims, No Drawings

INHIBITORS OF METALLOPROTEINASES

This application is the National Phase of International Application PCT/GB00/02085 filed May 31, 2000 which designated the U.S. and that International Application was published under PCT Article 21(2) in English.

The present invention relates to compounds useful in the inhibition of metalloproteinases and in particular to pharmaceutical compositions comprising these, as well as their use.

The compounds of this invention are inhibitors of one or more metalloproteinase enzymes. Metalloproteinases are a superfamily of proteinases (enzymes) whose numbers in recent years have increased dramatically. Based on structural and functional considerations these enzymes have been classified into families and subfamilies as described in N. M Hooper (1994) FEBS Letters 354:1–6. Examples of metalloproteinases include the matrix metalloproteinases (MMP) such as the colagenases (MMP1, MMP8, MMP13), the gelatinases (MMP2, MMP9), the stromelysins (MMP3, MMP10, MMP11), matrilysin (MMP7), metalloelastase (MMP12) enamelysin (MMP19), the MT-MMPs (MMP14, MMP15, MMP16, MMP17); the reprolysin or adamalysin or MDC family which includes the secretases and sheddases such as TNF converting enzymes (ADAM10 and TACE); the astacin family which include enzymes such as procollagen processing proteinase (PCP); and other metalloproteinases such as aggrecanase, the endothelin converting enzyme family and the angiotensin converting enzyme family.

Metalloproteinases are believed to be important in a plethora of physiological disease processes that involve tissue remodelling such as embryonic development, bone formation and uterine remodelling during menstruation. This is based on the ability of the metalloproteinases to cleave a broad range of matrix substrates such as collagen, proteoglycan and fibronectin. Metalloproteinases are also believed to be important in the processing, or secretion, of biological important cell mediators; such as tumour necrosis factor (TNF); and the post translational proteolysis processing, or shedding, of biologically important membrane proteins, such as the low affinity IgE receptor CD23 (for a more complete list see N. M. Hooper et al., (1997) Biochem J. 321:265–279).

Metalloproteinases have been associated with many disease conditions. Inhibition of the activity of one or more metalloproteinases may well be of benefit in these disease conditions, for example: various inflammatory and allergic diseases such as, inflammation of the joint (especially rheumatoid arthritis, osteoarthritis and gout), inflammation of the gastro-intestinal tract (especially inflammatory bowel-disease, ulcerative colitis and gastritis), inflammation of the skin (especially psoriasis, eczema, dermatitis); in tumour metastasis or invasion; in disease associated with uncontrolled degradation of the extracellular matrix such as osteoarthritis; in bone resorptive disease (such as osteoporosis and Paget's disease)); in diseases associated with aberrant angiogenesis; the enhanced collagen remodelling associated with diabetes, periodontal disease (such as gingivitis), corneal ulceration, ulceration of the skin, post-operative conditions (such as colonic anastomosis) and dermal wound healing; demyelinating diseases of the central and peripheral nervous systems (such as multiple sclerosis); Alzheimer's disease; and extracellular matrix remodelling observed in cardiovascular diseases such as restenosis and atheroscelerosis.

A number of metalloproteinase inhibitors are known; different classes of compounds may have different degrees of potency and selectivity for inhibiting various metalloproteinases. We have discovered a new class of compounds that are inhibitors of metalloproteinases and are of particular interest in inhibiting MMP-13. The compounds of this invention have beneficial potency and/or pharmacokinetic properties.

MMP13, or collagenase 3, was initially cloned from a cDNA library derived from a breast tumour [J. M. P. Freije et al. (1994) Journal of Biological Chemistry 269(24): 16766–167731]. PCR-RNA analysis of RNAs from a wide range of tissues indicated that MMP13 expression was limited to breast carcinomas as it was not found in breast fibroadenomas, normal or resting mammary gland, placenta, liver, ovary, uterus, prostate or parotid gland or in breast cancer cell lines (T47-D, MCF-7 and ZR75-1). Subsequent to this observation MMP13 has been detected in transformed epidermal keratinocytes [N. Johansson et al., (1997) Cell Growth Differ. 8(2):243–250], squamous cell carcinomas [N. Johansson et al., (1997) Am. J. Pathol. 151(2):499–508] and epidermal tumours [K Airola et al., (1997) J. Invest. Dermatol. 109(2):225–231]. These results are suggestive that MMP13 is secreted by transformed epithelial cells and may be involved in the extracellular matrix degradation and cell-matrix interaction associated with metastasis especially as observed in invasive breast. cancer lesions and in malignant epithelia growth in skin carcinogenesis.

Recent published data implies that MMP13 plays a role in the turnover of other connective tissues. For instance, consistent with MMP13's substrate specificity and preferential to degrade type II collagen [P. G. Mitchell et al., (1996) J. Clin. Invest. 97(3):761–768; V. Knauper et al., (1996) The Biochemical Journal 271:1544–1550], MMP13 has been hypothesised to serve a role during primary ossification and skeletal remodelling [M. Stahle-Backdahl et al., (1997) Lab. Invest. 76(5):717–728; N. Johannson et al., (1997) Dev. Dyn. 208(3):387–397], in destructive joint diseases such as rheumatoid and osteo-arthritis [D. Wernicke et al., (1996) J. Rheumatol. 23:590–595; P. G. Mitchell et al., (1996) J. Clin. Invest. 97(3):761–768; O. Lindy et al., (1997) Arthritis Rheum 40(8):1391–1399]; and during the aseptic loosening of hip replacements [S. Imai et al., (1998) J. Bone Joint Surg. Br. 80(4):701–710]. MMP13 has also been implicated in chronic adult periodontitis as it has been localised to the epithelium of chronically inflamed mucosa human gingival tissue [V. J. Uitto et al., (1998) Am. J. Pathol 152(6):1489–1499] and in remodelling of the collagenous matrix in chronic wounds [M. Vaalamo et al., (1997) J. Invest. Dermatol. 109(1):96–101].

MMP9 (Gelatinase B; 92 kDa Type IV Collagenase; 92 kDa Gelatinase) is a secreted protein which was first purifed, then cloned and sequenced, in 1989 (S. M. Wilhelm et al (1989) J. Biol Chem. 264 (29): 17213–17221. Published erratum in J. Biol Chem. (1990) 265(36):22570.). A recent review of MMP9 provides an excellent source for detailed information and references on this protease: T. H. Vu & Z. Werb (1 998) (In: Matrix Meteloproteinases. 1998. Edited by W. C. Parks & R. P. Mecham. pp 115–148. Academic Press. ISBN 0-12-545090-7). The following points are drawn from that review by T. H. Vu & Z. Werb (1998).

The expression of MMP9 is restricted normally to a few cell types, including trophoblasts, osteoclasts, neutrophils and macrophages. However, its expression can be induced in these same cells and in other cell types by several mediators, including exposure of the cells to growth factors or cytokines. These are the same mediators often implicated in initiating an inflammatory response. As with other secreted MMPs, MMP9 is released as an inactive pro-enzyme which is subsequently cleaved to form the enzymatically active enzyme. The proteases required for this activation in vivo are not known. The balance of active MMP9 versus inactive enzyme is further regulated in vivo by interaction with TIMP-1 (Tissue Inhibitor of Metalloproteinases-1), a naturally-occurring protein. TIMP-1 binds to the C-terminal region of MMP9, leading to inhibition of the catalytic domain of MMP9. The balance of induced expression of ProMMP9, cleavage of Pro- to active MMP9 and the presence of TIMP-1 combine to determine the amount of catalytically active MMP9 which is present at a local site. Proteolytically active MMP9 attacks substrates which include gelatin, elastin, and native Type IV and Type V collagens; it has no activity against native Type I collagen, proteoglycans or laminins.

There has been a growing body of data implicating roles for MMP9 in various physiological and pathological processes. Physiological roles include the invasion of embryonic trophoblasts through the uterine epithelium in the early stages of embryonic implantation; some role in the growth and development of bones; and migration of inflammatory cells from the vasculature into tissues. Increased MMP9 expression has been observed in certain pathological conditions, thereby implicatinag MMP9 in disease processes such as arthritis, tumour metastasis, Alzheimer's, Multiple Sclerosis, and plaque rupture in atherosclerosis leading to acute coronary conditions such as Myocardial Infarction.

In a first aspect of the invention we provide compounds of the formula I wherein ring B is a monocyclic or bicyclic alkyl, aryl, aralkyl, heteroaryl or heteroaralkyl ring comprising up to 12 ring atoms and containing one or more heteroatoms independently chosen from N, O, and S; alternatively ring B may be biphenyl; ring B may optionally be linked to ring A by a C1–4 alkyl or a C1–4 alkoxy chain linking the 2-position of ring B with a carbon atom alpha to X2;

each R3 is independently selected from hydrogen, halogen, NO2, COOR wherein R is hydrogen or C1–6alkyl, CN, CF3, C1–6 alkyl, —S—C1–6 alkyl, —SO—C1–6 alkyl, —SO2-C1–6 alkyl, C1–6 alkoxy and up to C10 aryloxy, n is 1,2 or 3;

P is —(CH$_2$)n- wherein n=0, 1, 2, or P is an alkene or alkyne chain of up to six carbon atoms; where X2 is C, P may be -Het-, —(CH[R6])n-Het-, -Het-(CH[R6]n- or -Het-(CH[R6])n-Het-, wherein Het is selected from —CO—, —S—, SO—, —SO2-, —NR6-, or —O—wherein n is 1 or 2, or P may be selected from —CO—N(R6)-, —N(R6)-CO—, —SO2-N(R6)- and —N(R6)-SO2-, and R6 is hydrogen, C1–6 alkyl, up to C10 aralkyl or up to C9 heteroalkyl;

Ring A is a 5–7 membered aliphatic ring and may optionally be mono- or di-substituted by optionally substituted C1–6 alkyl or C1–6 alkoxy, each substituent being independently selected from halogen, C1–6 alkyl or an oxo group;

X1 and X2 are independently selected from N and C, where a ring substituent on ring A is an oxo group this is preferably adjacent a ring nitrogen atom;

Y is selected from —SO2- and —CO—;

Z is —CONHOH, Y is —CO— and Q is selected from —C(R6)(R7)-, —C(R6)(R7)-CH2-, —N(R6)-, and —N(R6)-CH2- wherein R6 is as defined above, and solely in relation to Q as here defined, R6 may also represent up to C10 aryl and up to C9 heteroaryl, and R7 is H, C1–6 alkyl, or together with R6 forms a carbocyclic or heterocyclic spiro 5, 6 or 7 membered ring, the latter containing at least one heteroatom selected from N, O, and S;

Z is —CONHOH, Y is —SO02- and Q is selected from —C(R6)(R7)-, and —C(R6)(R7)-CH2-;

or Z is —N(OH)CHO and Q is selected from —CH(R6)-, —CH(R6)-CH2-, and —N(R6)-CH2-;

R1 is H, or C1–6 alkyl;

Z is selected from —COOH, —CONHOH, —N(OH)CHO and N(OH)COR wherein R is C1–6alkyl, up to C10 aryl and up to C9 aralkyl and R2 is a heterocyclylalkyl ring having 5–7 ring atoms and comprising one or two ring heteroatoms independently selected from oxygen, nitrogen and sulphur, the ring being optionally substituted by (i) Y—R9 wherein R9 is C1–6 alkyl, up to C10 aryl, up to C12 aralkyl or up to C12 heteroaryl(hetero)aikyl, or (ii) Y-T-R9 wherein Y and R9 are as previously defined and T is oxygen or N—R8 wherein R8 is hydrogen or C1–6 alkyl, the heteroatom(s) being independently selected from oxygen, nitrogen and sulphur, R9 and R8 independently being optionally substituted by one or two groups selected from halogen, NO2, CN, CF3, C1–6 alkyl, —S—C1–6 alkyl, —SO—C1–6 alkyl, —SO2-C1–6 alkyl and C1–6 alkoxy.

Any alkyl groups outlined above may be straight chain or branched.

Convenient values for the above groups include the following:

ring A=a 5–6 membered aliphatic ring, such as a piperazine or piperidine ring, and may optionally be mono- or di-substituted by optionally substituted C1–6 alkyl or C1–6 alkoxy, each substituent being independently selected from halogen, C1–6 alkyl or an oxo group;

R3=hydrogen, halogen, NO2, CF3, C1–4 alkyl, and C1–4 alkoxy, n is 1 or 2, such as individually 4-fluoro, CF3, 4-chloro and 3,4-dichloro;.

ring B=monocyclic or bicyclic cycloalkyl, aryl, aralkyl or heteroaryl having up to 10 ring atoms, especially monocyclic aryl, aralkyl or heteroaryl having up to 7 ring atoms, more especially monocyclic aryl or heteroaryl having, up to 6 ring atoms, such as a phenyl or pyridyl ring;

P=—(CH2)n- wherein n is 0 or 1, or P is —NH—CO— one or both of X2 and X1=N

Y=—SO2- or —CO—;

Q=—CH(R6)-, —CH(R6)-CH2-, —N(R6)-, and —N(R6)-CH2- wherein R6 is hydrogen or

C1–6 alkyl; when Q=—N(R6)-, or —N(R6)-CH2- then Y may also be —CS—; especially

Q=—CH(R6)- wherein R6 is hydrogen or C1–4 alkyl such as propyl or butyl, particularly propyl; also where Q is linked to R1 or R2 to form a 5–7 alkyl or heteroalkyl ring such as a cyclohexyl ring;

R1=hydrogen, or C1–4 alkyl.

Z=—CONHOH— or —N(OH)CHO and R2 is a heterocyclylalkyl ring having 5–7 ring atoms and comprising one or two ring heteroatoms independently selected from oxygen, nitrogen and sulphur, the ring being optionally substituted by (i) Y—R9 wherein R9 is C1–6 alkyl, up to C10 aryl, up to C12 aralkyl or up to C12 heteroaryl(hetero)alkyl, or (ii) Y-T-R9 wherein Y and R9 are as previously defined and T is oxygen or N—R8 wherein R8 is hydrogen or C1–6alkyl, the heteroatom(s) being independently selected from oxygen, nitrogen and sulphur, R9 and R8 independently being optionally substituted by one or two groups selected from halogen, NO2, CN, CF3, C1–6 alkyl, —S—C1–6 alkyl, —SO—C1–6 alkyl, —SO2-C1–6 alkyl and C1–6 alkoxy.

Preferred values for the above groups include the following:

R3=hydrogen, chlorine, fluorine, NO2, CF3, methyl, ethyl, methoxy, ethoxy, particularly methoxy or fluorine;

ring B=phenyl, biphenyl, napthyl, pyridyl, pyrimidinyl, pyrazinyl and pyridazinyl, especially phenyl or pyridyl, more especially phenyl or 2-pyridyl;

ring A =piperazine;

P=a direct bond;

both X2 and X1 are N;

Y=—SO2-;

Q=—CH2-;

R2 is a hetcrocyclylalkyl ring having 5–7 ring atoms and comprising one or two ring heteroatoms independently selected from oxygen, nitrogen and sulphur, the ring being optionally substituted by (i) Y—R9 wherein Y is —SO2- or —CO— and R9 is C1–6 alkyl or alkylamino, up to C10 aryl or arylamino, up to C12 aralkyl or aralkylamino or up to C12 heteroaryl(hetero)alkyl, R9 independently being optionally substituted by one or two groups selected from halogen, NO2, CN, CF3, C1–6 alkyl, —S—C1–6 alkyl, —SO—C1–6 alkyl, —SO2-C1–6 alkyl and C1–6 alkoxy;

R1 is hydrogen;

Z is —N(OH)CHO;

More preferred values include:

R3 being methoxy, fluorine or 4-fluoro;

ring A is unsubstituted;

ring B is phenyl, pyridyl, or 2-pyridyl;

R2 is 3- or 4-piperidinyl, optionally N-substituted by Y—R9 wherein Y is —SO2- or —CO— and R9 is C1–4 alkyl or alkylamino, C6 aryl or arylamino, up to C10 aralkyl or aralkylamino or up to C10 heteroaryl(hetero)alkyl, R9 independently being optionally substituted by one or two groups selected from halogen, CF3, and C1–4 alkyl;

Preferred combinations of Rings A and B include phenyl and piperazinyl; pyridyl and piperazinyl respectively.

Particular compounds include those where Ring A is unsubstituted.

Particular alicyclic, fused and heterocyclic rings for ring B include any one of

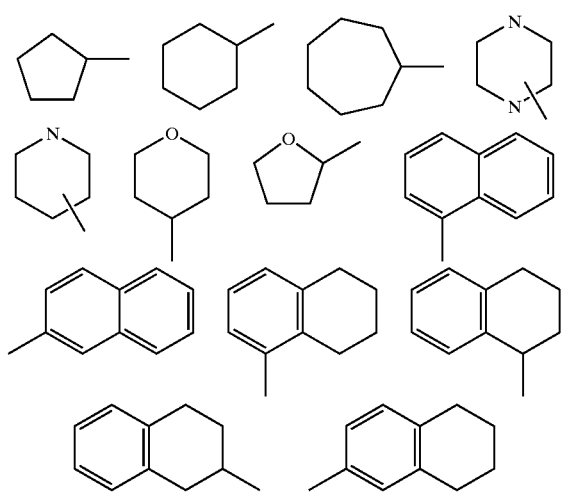

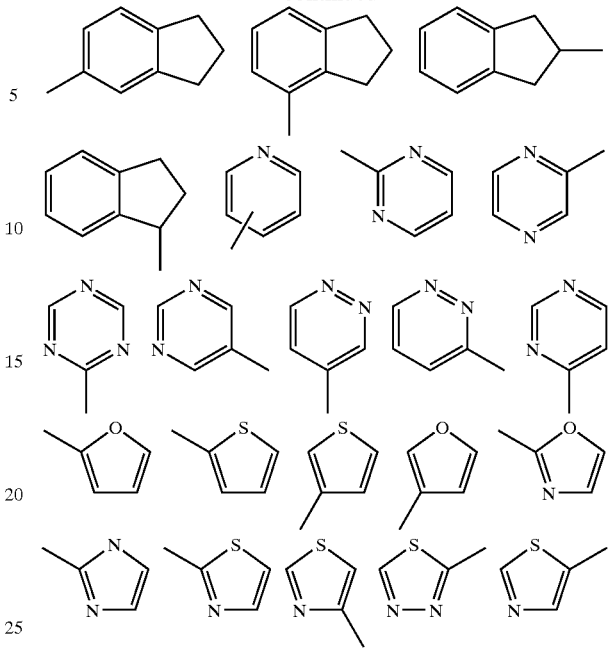

Particular rings for ring A include any one of

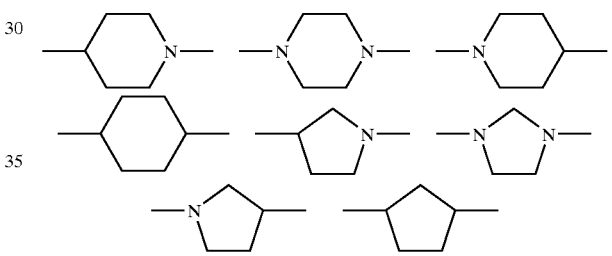

and its corresponding seven membered analogue(s).

It will be appreciated that the particular substitituents and number of substituents on rings A and B are selected so as to avoid sterically undesirable combinations.

Where optically active centres exist in the compounds of formula I, we disclose all individual optically active forms and combinations of these as individual specific embodiments of the invention, as well as their corresponding racemates.

The above compounds are potent MMP13 inhbitors, they also have good aggrecanase activity. As previously outlined the compounds of the invention are metalloproteinase inhibitors, in particular they are inhibitors of MMP13. Each of the above indications for the compounds of the formula I represents an independent and particular embodiment of the invention. Whilst we do not wish to be bound by theoretical considerations, the compounds of the invention are believed to show selective inhibition for any one of the above indications relative to any MMP1 inhibitory activity, by way of non-limiting example they may show 100–1000 fold selectivity over any MMP1 inhibitory activity.

The compounds of the invention may be provided as pharmaceutically acceptable salts. These include acid addition salts such as hydrochloride, hydrobromide, citrate and maleate salts and salts formed with phosphoric and sulphuric acid. In another aspect suitable salts are base salts such as an alkali metal salt for example sodium or potassium, an alkaline earth metal salt for example calcium or magnesium, or organic amine salt for example triethylamine.

They may also be provided as in vivo hydrolysable esters. These are pharmaceutically acceptable esters that hydrolyse in the human body to produce the parent compound. Such esters can be identified by administering, for example intravenously to a test animal, the compound under test and subsequently examining the test animal's body fluids. Suitable in vivo hydrolysable esters for carboxy include methoxymethyl and for hydroxy include acetyl.

In order to use a compound of the formula (I) or a pharmaceutically acceptable salt or in vivo hydrolysable ester thereof for the therapeutic treatment (including prophylactic treatment) of mammals including humans, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or an in vivo hydrolysable ester and pharmaceutically acceptable carrier.

The pharmaceutical compositions of this invention may be administered in standard manner for the disease condition that it is desired to treat, for example by oral, topical, parenteral, buccal, nasal, vaginal or rectal adminstration or by inhalation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oil solutions or suspensions or sterile emulsions.

In addition to the compounds of the present invention the pharmaceutical composition of this invention may also contain, or be co-administered (simultaneously or sequentially) with, one or more pharmacological agents of value in treating one or more disease conditions referred to hereinabove.

The pharmaceutical compositions of this invention will normally be administered to humans so that, for example, a daily dose of 0.5 to 75 mg/kg body weight (and preferably of 0.5 to 30 mg/kg body weight) is received. This daily dose may be given in divided doses as necessary, the precise amount of the compound received and the route of administration depending on the weight, age and sex of the patient being treated and on the particular disease condition being treated according to principles known in the art.

Typically unit dosage forms will contain about 1 mg to 500 mg of a compound of this invention.

Therefore in a further aspect, the present invention provides a compound of the formula (I) or a pharmaceutically acceptable salt or in vivo hydrolysable ester thereof for use in a method of therapeutic treatment of the human or animal body.

In yet a further aspect the present invention provides a method of treating a metalloproteinase mediated disease condition which comprises administering to a warm-blooded animal a therapeutically effective amount of a compound of the formula (I) or a pharmaceutically acceptable salt or in vivo hydrolysable ester thereof.

In another aspect the present invention provides a process for preparing a compound of the formula (I) or a pharmaceutically acceptable salt or in vivo hydrolysable ester thereof which process comprises a) reacting a compound of the formula (II) or a pharmaceutically acceptable salt or in vivo hydrolysable ester thereof with a compound of the formula (III)

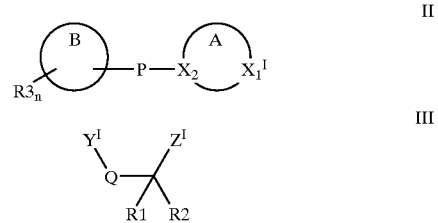

wherein $X_1^1$ represents X or a precursor of X (whether by modification or displacement) or an activated form of X suitable for reaction with $Y_1$;

$Y_1$ represents Y, a precursor of Y, or an activated form of Y suitable for reaction with $X_1^1$;

by way of non-limiting example, when X is C then $X_1$ may be derivatised to include a precursor of Y for reaction with a compound of formula III wherein $Y^1$ is a precursor of Y;

$Z^1$ represents a protected form of Z, a precursor of Z (whether by modification or displacement of $Z^1$) or an activated form of Z; or b) reacting a compound of the formual (IV)) or a pharmaceutically acceptable salt or in vivo hydrolysable ester thereof with a compound of the formula (V).

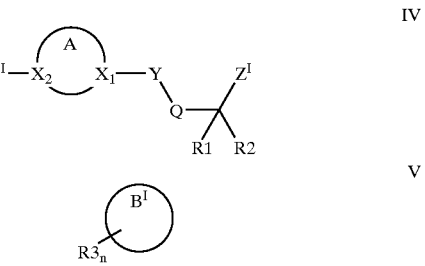

wherein $B^1$ represents a suitable ring function or substituent group for reaction with $P^i$;

$Z^1$ is as hereinbefore defined; and $P^i$ represents a suitably activated form of the linker P for reaction with $B^1$; or c) reacting a compound of the general formula (VIII)

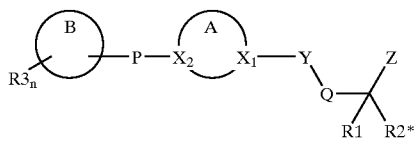

wherein R2* is a precursor for R2 with appropriate reagent(s) in one or more steps to yield R2. The group Z is conveniently protected during such steps. By way of non-limiting example R2* is a piperidine or piperazine ring; or (d) reacting a compound of the formula IX with an appropriate compound of the formula R1-CO—R2 to yield an alkene of the formula X, which is then converted to a compound of the formula XI wherein Z* is a hydroxylamine precursor of the group Z, and then converting Z* to the group Z, all as set out below:

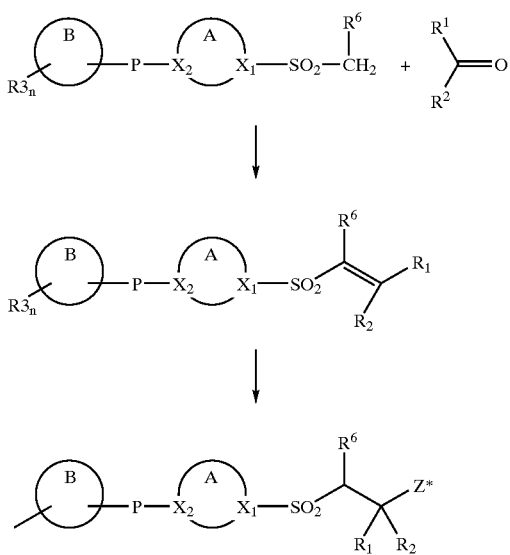

A compound of the formula (II) is conveniently prepared by reacting a compound of the formula (VI) with a compound of the formula (VII)

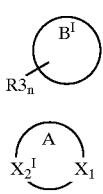

wherein $B^1$ represents a suitable ring function or substituent group, $X_2^1$ represents X or a precursor of X (whether by modification or displacement) or an activated form of X suitable for reaction with $B^1$ and wherein $B^1$ and $X_2^1$ when reacted together provide the tinker P between ring B and ring A in the compound of formula (II). By way of non-limiting example, when $X_2$ is N then ring A is suitably derivatised to introduce the linker P via $B^1$, and when $X_2$ is C then both ring A and ring are suitably derivatised to provide the linker P by the reaction of $B^1$ and $X_2^1$.

Convenient commercially available starting materials include

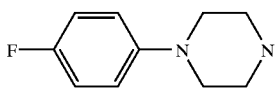

The compounds of the invention may be evaluated for example in any one of the following assays:
Isolated Enzyme Assays:
Matrix Metalloproteinase Family, Including for Example MMP13

Recombinant human proMMP13 may be expressed and purified as described by Knauper et al. [V. Knauper et al., (1996) The Biochemical Journal 271:1544–1550 (1996)]. The purified enzyme can be used to monitor inhibitors of activity as follows: purified proMMP13 is activated using 1 mM amino phenyl mercuric acid (APMA), 20 hours at 21° C.; the activated MMP13 (11.25 ng per assay) is incubated for 4–5 hours at 35° C. in assay buffer (0.1M Tris-HCl, pH 7.5 containing 0.1M NaCl, 20 mM $CaCl_2$, 0.02 mM ZnCl and 0.05% (w/v) Brij 35 using the synthetic substrate 7-methoxycoumarin-4-yl)acetyl.Pro.Leu.Gly.Leu.N-3-(2,4-dinitrophenyl)-L-2,3 diaminopropionyl.Ala.Arg.$NH_2$ in the presence or absence of inhibitors. Activity is determined by measuring the fluorescence at λex 328 nm and λem 393 nm. Percent inhibition is calculated as follows: % Inhibition is equal to the [Fluorescence$_{plus\ inhibitor}$−Fluorescence$_{background}$] divided by the [Fluorescence$_{minus\ inhibitor}$−Fluorescence$_{background}$].

A similar protocol can be used for other expressed and purified pro MMPs using substrates and buffers conditions optimal for the particular MMP, for instance as described in C. Graham Knight et al., (1992) FEBS Lett. 296(3): 263–266.

Adamalysin Family, Including for Example TNF Convertase.

The ability of the compounds to inhibit pro TNFα convertase enzyme may be assessed using a partially purified, isolated enzyme assay, the enzyme being obtained from the membranes of THP-1 as described by K. M. Mohler et al., (1994) Nature 370:218–220. The purified enzyme activity and inhibition thereof is determined by incubating the partially purfied enzyme in the presence or absence of test compounds using the substrate 4',5'-Dimethoxyfluoresceinyl Ser.Pro.Leu.Ala.Gln.Ala.Val.Arg.Ser.Ser.Ser.Arg.Cys(4-(3-succinimid-1-yl)-fluorescein)-$NH_2$ in assay buffer (50 mM Tris HCl, pH 7.4 containing 0.1% (w/v) Triton X-100 and 2 mM $CaCl_2$), at 26° C. for 18 hours. The amount of inhibition is determined as for MMP13 except λex 490 nm and λem 530 nm were used. The substrate was synthesised as follows. The peptidic part of the substrate was assembled on Fmoc-NH-Rink-MBHA-polystyrene resin either manually-or on an automated peptide synthesiser by standard methods involving the use of Fmoc-amino acids and O-benzotriazol-1-yl-N,N,N',N'-tetramethyluronium hexafluorophosphate (HBTU) as coupling agent with at least a 4- or 5-fold excess of Fmoc-amino acid and HBTU. $Ser^1$ and $Pro^2$ were double-coupled. The following side chain protection strategy was employed; $Ser^1(Bu^t)$, $Gln^5$(Trityl), $Arg^{8,12}$(Pmc or Pbf), $Ser^{9,10,11}$(Trityl), $Cys^{13}$(Trityl). Following assembly, the N-terminal Fmoc-protecting group was removed by treating the Fmoc-peptidyl-resin with in DMF. The amino-peptidyl-resin so obtained was acylated by treatment for 1.5–2 hr at 70° C. with 1.5–2 equivalents of 4',5'-dimethoxyfluorescein-4(5)-carboxylic acid [Khanna & Ullman, (1980) Anal Biochem. 108:156–161) which had been preactivated with diisopropylcarbodiimide and 1-hydroxybenzotriazole in DMF]. The dimethoxyfluoresceinyl-peptide was then simultaneously deprotected and cleaved from the resin by treatment with trifluoroacetic acid containing 5% each of water and triethylsilane. The dimethoxyfluoresceinyl-peptide was isolated by evaporation, trituration with diethyl ether and filtration. The isolated peptide was reacted with 4-(N-maleimido)-fluorescein in DMF containing diisopropylethylamine, the product purified by RP-HPLC and finally isolated by freeze-drying from aqueous acetic acid. The product was characterised by MALDI-TOF MS and amino acid analysis.

Natural Substrates

The activity of the compounds of the invention as inhibitors of aggrecan degradation may be assayed using methods for example based on the disclosure of E. C. Arner et al., (1998) Osteoarthritis and Cartilage 6:214–228 and the antibodies described therein. The potency of compounds to act as inhibitors against collagenases can be determined as described by T. Cawston and A. Barrett (1979) Anal. Biochem. 99:340–345.

Inhibition of Metlloproteinase Activity in Cell/Tissue Based Activity:

Test as an Agent to Inhibit Membrane Sheddases Such as TNF Convertase

The ability of the compounds of this invention to inhibit the cellular processing of TNFα production may be assessed in THP-1 cells using an ELISA to detect released TNF essentially as described K. M. Mohler et al., (1994) Nature 370:218–220. In a similar fashion the processing or shedding of other membrane molecules such as those described in N. M. Hooper et al., (1997) Biochem. J. 321:265–279 maybe tested using appropriate cell lines and with suitable antibodies to detect the shed protein.

Test as an Agent to Inhibit Cell Based Invasion

The ability of the compound of this invention to inhibit the migration of cells in an invasion assay may be determined as described in A. Albini et al., (1987) Cancer Research 47:3239–3245.

Test as an Agent to Inhibit Whole Blood TNF Sheddase Activity

The ability of the compounds of this invention to inhibit TNFα production is assessed in a human whole blood assay where LPS is used to stimulate the release of TNFα. Heparinized (10 Units/ml) human blood obtained from volunteers is diluted 1:5 with medium (RPMI1640 +bicarbonate, penicillin, streptomycin and glutamine) and incubated (160 µl) with 20 µl of test compound (triplicates), in DMSO or appropriate vehicle, for 30 min at 37° C. in a humidified (5% $CO_2$/95% air) incubator, prior to addition of 20 µl LPS (*E. coli.* 0111:B4; final concentration 10 µg/ml). Each assay includes controls of diluted blood incubated with medium alone (6 wells/plate) or a known TNFα inhibitor as standard. The plates are then incubated for 6 hours at 37° C. (humidified incubator), centrifuged (2000 rpm for 10 min; 4° C.), plasma harvested (50–100 µl) and stored in 96 well plates at −70° C. before subsequent analysis for TNFα concentration by ELISA.

Test as an Agent to Inhibit In Vitro Cartilage Degradation

The ability of the compounds of this invention to inhibit the degradation of the aggrecan or collagen components of cartilage can be assessed essentially as described by K. M. Bottdmley et al., (1997) Biochem J. 323:483–488.

Pharmacodynamic Test

To evaluate the clearance properties and bioavailability of the compounds of this invention an ex vivo pharmacodynamic test is employed which utilises the synthetic substrate assays above or alternatively HPLC or Mass spectrometric analysis. This is a generic test which can be used to estimate the clearance rate of compounds across a range of species. Animals (e.g. rats, marmosets) are dosed iv or po with a soluble formulation of compound (such as 20% w/v DMSO, 60% w/v PEG400) and at subsequent time points (e.g. 5, 15, 30, 60, 120, 240, 480, 720, 1220 mins) the blood samples are taken from an appropriate vessel into 10 U heparin. Plasma fractions are obtained following centrifugation and the plasma proteins precipitated with acetonitrile (80% w/v final concentration). After 30 mins at −20° C. the plasma proteins are sedimented by centrifugation and the supernatant fraction is evaporated to dryness using a Savant speed vac. The sediment is reconstituted in assay buffer and subsequently analysed for compound content using, the synthetic substrate assay. Briefly, a compound concentration-response curve is constructed for the compound undergoing evaluation. Serial dilutions of the reconstituted plasma extracts are assessed for activity and the amount of compound present in the original plasma sample is calculated using the concentration-response curve taking into account the total plasma dilution factor.

In Vivo Assessment

Test as an Anti-TNF Agent

The ability of the compounds of this invention as ex vivo TNFα inhibitors is assessed in the rat. Briefly, groups of male [Wistar Alderley Park (AP)) rats (180–210 g) are dosed with compound (6 rats) or drug vehicle (10 rats) by the appropriate route e.g. peroral (p.o.), intraperitoneal (i.p.), subcutaneous (s.c.). Ninety minutes later rats are sacrificed using a rising concentration of $CO_2$ and bled out via the posterior vena cavae into 5 Units of sodium heparin/ml blood. Blood samples are immediately placed on ice and centrifuged at 2000 rpm for 10 min at 4° C. and the harvested plasmas frozen at −20° C. for subsequent assay of their effect on TNFα production by LPS-stimulated human blood. The rat plasma samples are thawed and 175 µl of each sample are added to a set format pattern in a 96 U well plate. Fifty µl of heparinized human blood is then added to each well, mixed and the plate is incubated for 30 min at 37° C. (humidified incubator). LPS (25 µl; final concentration 10 µg/ml) is added to the wells and incubation continued for a further 5.5 hours. Control wells are incubated with 25 µl of medium alone. Plates are then centrifuged for 10 min at 2000 rpm and 200 µl of the supernatants are transferred to a 96 well plate and frozen at −20° C. for subsequent analysis of TNF concentration by ELISA.

Data analysis by dedicated software calculates for each compound/dose:

Percent inhibition of TNFα=Mean TNFα (Controls)−Mean TNFα (Treated)×100/Mean TNFα (Controls)

Test as an Anti-Arthritic Agent

Activity of a compound as an anti-arthritic is tested in the collagen-induced arthritis (CIA) as defined by D. E. Trentham et al., (1977) J. Exp. Med. 146:857. In this model acid soluble native type II collagen causes polyarthritis in rats when administered in Freunds incomplete adjuvant. Similar conditions can be used to induce arthritis in mice and primates.

Test as an Anti-Cancer Agent

Activity of a compound as an anti-cancer agent may be assessed essentially as described in I. J. Fidler (1978) Methods in Cancer Research 15:399–439, using for example the B16 cell line (described in B. Hibner et al., Abstract 283 p 75 10th NCI-EORTC Symposium, Amsterdam Jun. 16–19, 1998).

The invention will now be illustrated but not limited by the following Examples:

EXAMPLES

Example 1

Acetic anhydride (1 ml) was added dropwise to formic acid (3 ml) at 0° C. and the mixture was stirred at 0° C. for 30 minutes. This mixture was added dropwise to a solution of 4-(4-fluorophenyl)-1-[2-(1-phenethylcarbonylpiperidin-4-yl)-2-hydroxylaminoethylsuphonyl]-piperazine (0.65 g) in tetrahydrofuran (5 ml) at 0° C. and the mixture was allowed to warm to ambient temperature and was stirred for 10 hours. The reaction mixture was evaporated to small volume, aqueous sodium bicarbonate was added and the mixture was extracted with ethyl acetate (2×25 ml).

The ethyl acetate extracts were dried and evaporated to dryness. The gum so obtained was subjected to chromatography on silica eluted initially with an ethyl acetate:isohexane mixture (3:2 v/v) and then an ethyl acetate;methanol mixture (9:1). There was obtained 4-(4-fluorophenyl)-1-[2-(1-phenethylcarbonylpiperidin-4-yl)-2-{O-formylhydroxylamino}ethylsuphonyl]-piperazine as a gum, yield 230 mg, M+H=547.

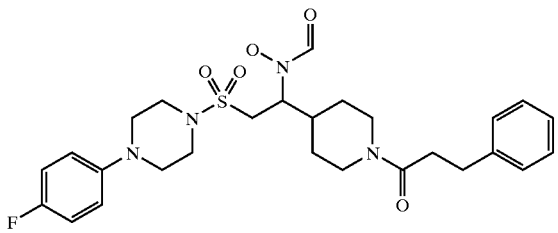

A mixture of 4-(4-fluorophenyl)-1-[2-(1-phenethylcarbonylpiperidin-4-yl)-ethenylsulphonyl]-piperazine (0.75 g) and 50% aqueous hydroxylamine (5 ml) in tetrahydrofuran (10 ml) was stirred for 48 hours. The mixture was evaporated to dryness and water (20 ml) was added. The mixture was extracted with ethyl acetate (2×15 ml) and the extracts were washed with water and dried. Removal of the solvent gave 4-(4-fluorophenyl)-1-[2-(1-phenethylcarbonylpiperidin-4-yl)-2-hydroxylaminoethylsuphonyl]-piperazine (0.65 g) as a gum, M+H=519 (518).

3-Phenylpropionyl chloride (0.21 ml) was added dropwise to a solution of 4-(4-fluorophenyl)-1-[2-(piperidin-4-yl)-ethenylsulphonyl]-piperazine (0.5 g) in dichloromethane containing triethylamine (0.2 ml). The mixture was stirred for 3 hours, evaporated to dryness, diluted with water and extracted with ethyl acetate (2×15 ml). The ethyl acetate extracts were combined and washed with aqueous sodium bicarbonate, water and dried. Removal of the solvent gave 4-(4-fluorophenyl)-1-[2-(1-phenethylcarbonylpiperidin-4-yl)-ethenylsulphonyl]-piperazine as a gum, M+H=486 (485).

A mixture of 4-(4-fluorophenyl)-1-[2-(1-t-butoxycarbonylpiperidin-4-yl)-ethenylsulphonyl]-piperazine (1.96 g) and trifluoroacetic acid (5 ml) was stirred at ambient temperature for 5 hours. The mixture was evaporated to dryness, diluted with water, basified with aqueous 2M sodium hydroxide and extracted with ethyl acetate (2×20 ml). Removal of the solvent gave 4-(4-fluorophenyl)-1-[2-(piperidin-4-yl)-ethenylsulphonyl]-piperazine.

In like manner using 4-(4-fluorophenyl)-1-[2-(1-t-butoxycarbonylpiperidin-4-yl)-2-{O-formylhydroxylamino}ethylsuphonyl]-piperazine as starting material there was obtained 4-(4-fluorophenyl)-1-[2-(piperidin-4-yl)]-2-{O-formylhydroxylamino}ethylsuphonyl]-piperazine, M+H=415.

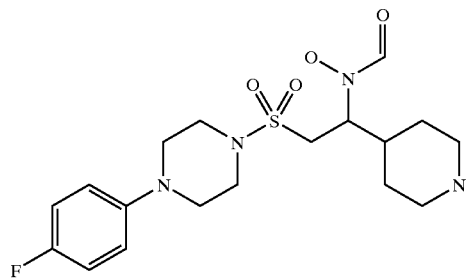

n-Butyl lithium (8.6 ml of a 1.6 M solution in THF) was added dropwise to a suspension of 4-(4-fluorophenyl)-1-methanesulphonylpiperazine (3.52 g) in THF (40 ml) at −78° C. and the mixture was stirred for 30 minutes. Diethylchlorophosphate (1.97 ml) was added dropwise and the mixture was stirred at −78° C. for a further 30 minutes. n-Butyl lithium (8.6 ml of a 1.6 M solution in THF) was added dropwise and stirred for 30 minutes. A solution of 1-(t-butoxycarbonyl)-piperidine-4-aldehyde (2.91 g) in THF (5 ml) was added dropwise and the mixture was allowed to warm to ambient temperature and was stired for 10 hours. Saturated aqueous ammonium chloride solution (5 ml) was added, the reaction mixture was diluted with ethyl acetate (25 ml) and washed with water. Removal of the solvent gave 4-(4-fluorophenyl)-1-[2-(1-t-butoxycarbonylpiperidin-4-yl)-ethenylsulphonyl]-piperazine as a gum which solidified on standing, M+H=455 (454).

Example 2

In like manner there were prepared compounds of the formula:

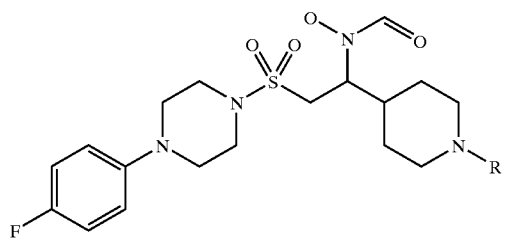

| R | M + H |
|---|---|
| —COOBu$^t$ | 515 |
| 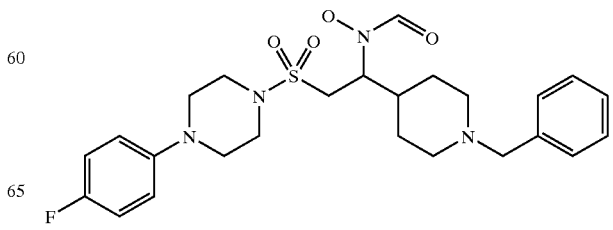 | 583 |

Example 3

Using procedures analogous to those outlined in Example 1 there were prepared:

-continued
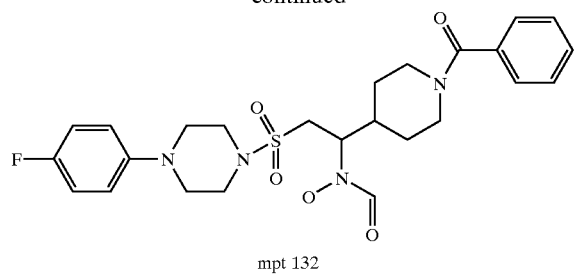
mpt 132
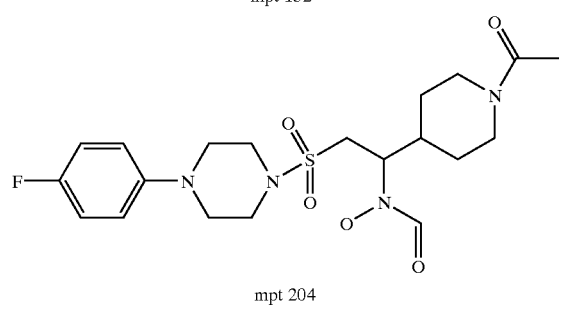
mpt 204
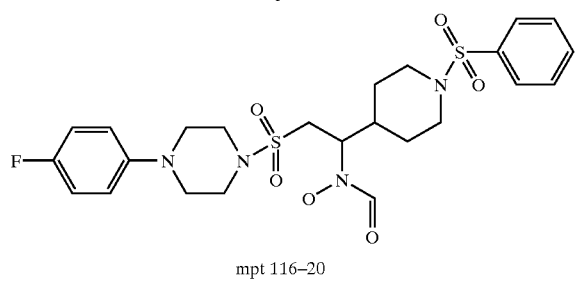
mpt 116–20
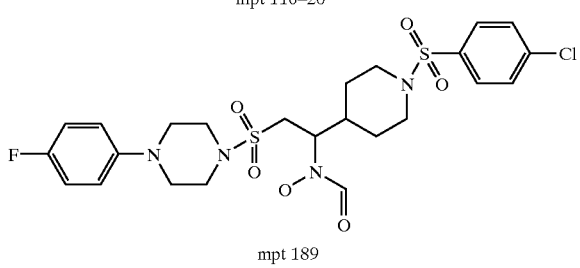
mpt 189
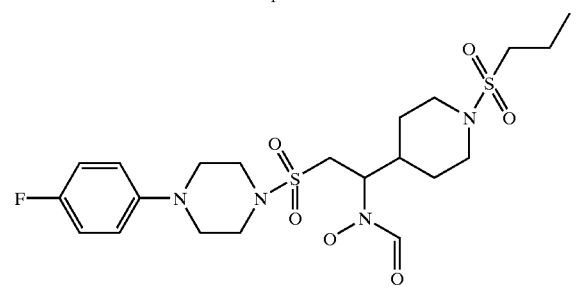
mpt 182
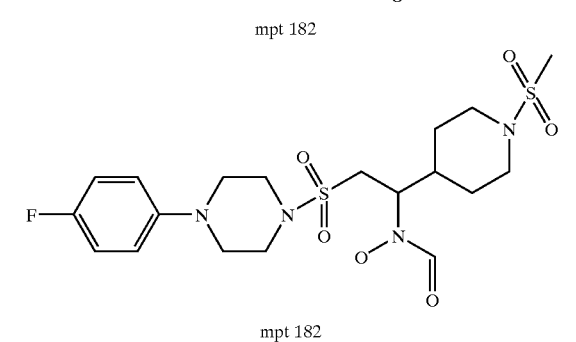
mpt 182
-continued
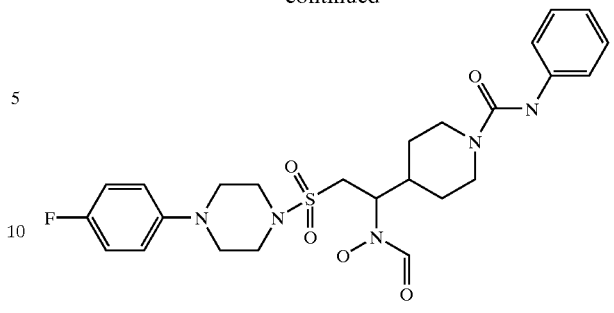
mpt 121
Example 4
Using procedures analogous to those outlined in Example 1 there were prepared:
| R | MPt ° C. | M + H |
|---|---|---|
| ![2-methylsulfonylphenyl] | | 589 |
| ![3-chlorophenylsulfonyl] | | 589 |
| ![3-trifluoromethylphenylsulfonyl] | | 623 |
| ![1-methyl-4-methylsulfonylimidazole] | | 559 |

-continued

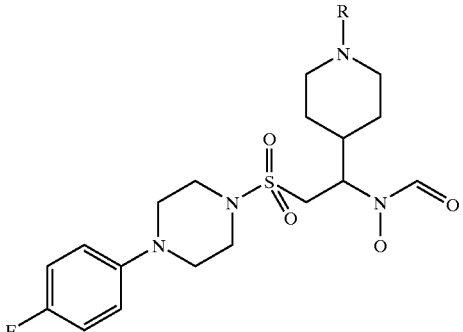

| R | MPt ° C. | M + H |
|---|---|---|
| 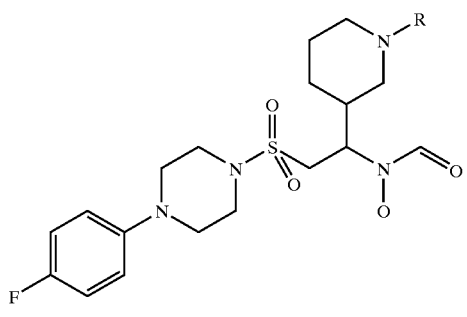 | | 641 |
| 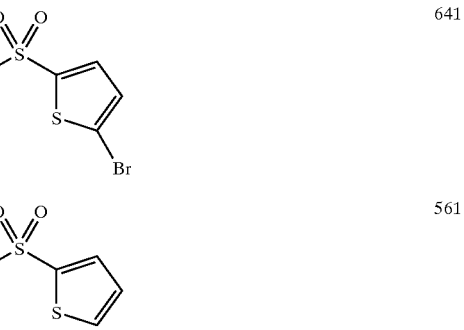 | | 561 |
| CF₃CH₂SO₂— | | 561 |
| iso-PrSO₂— | 170–172 | |
| PhCH₂NHCO— | 130 | |
| 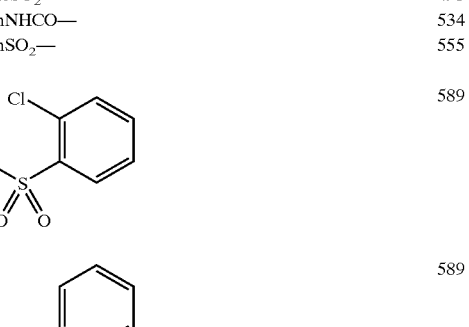 | 132 | |
| PhCH₂CH₂NHCO— | 124 | |
| iso-PrNHCO— | 155–158 | |

Example 5

Using procedures analogous to those outlined in Example 1 and using the starting material 1-(t-butoxycarbonyl)-3-formylpiperidine [CAS number 118156-93-7] there were prepared:

| R | MPt ° C. | M + H |
|---|---|---|
| PhCO— | | 519 |
| n-PrSO₂— | | 521 |

-continued

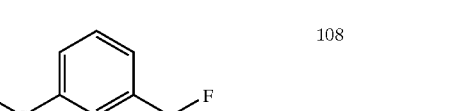

| R | MPt ° C. | M + H |
|---|---|---|
| MeSO₂— | | 493 |
| PhNHCO— | | 534 |
| PhSO₂— | | 555 |
| 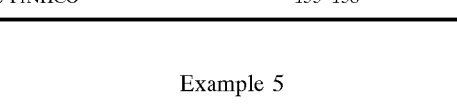 | | 589 |
|  | | 589 |
| 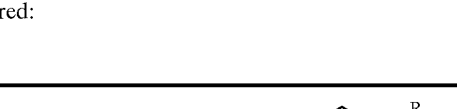 | 108 | |
|  | 105 | |
| 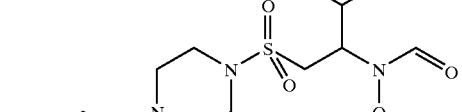 | | 561 |
| CF₃CH₂SO₂— | 87–90 | |
| iso-PrSO₂— | | 521 |
| PhCH₂NHCO— | 95–100 | |
|  | 110 | |
| PhCH₂CH₂NHCO— | 90 | |
| iso-PrNHCO— | 95–97 | |

-continued

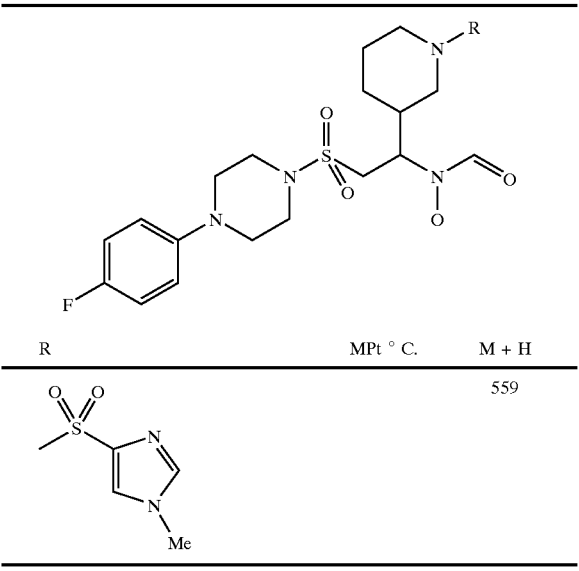

| R | MPt °C. | M + H |
|---|---|---|
| 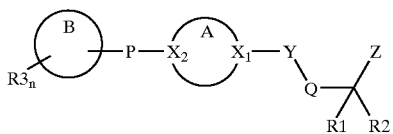 | | 559 |

I claim:

1. A compound of the formula I $$\text{R3}_n-\underset{B}{\bigcirc}-P-X_2-\underset{A}{\bigcirc}-X_1-Y-\underset{Q}{\overset{R1\ R2}{C}}-Z$$

I wherein ring B represents a pyridyl ring;

each R3 is independently selected from hydrogen, halogen, $NO_2$, COOR wherein R is hydrogen or $C_{1-6}$ alkyl, CN, $CF_3$, $C_{1-6}$ alkyl, —S—$Cl_6$ alkyl, —SO—$C_{1-6}$ alkyl, $C_{1-6}$ alkoxy and up to $C_{10}$ aryloxy, n is 1, 2, or 3;

P is —(CH$_2$)n- wherein n=0, 1, 2, or P is an alkene or alkyne chain of up to six carbon atoms;

Ring A represents a piperazinyl ring optionally mono- or di- substituted by a $C_{1-6}$ alkyl or $C_{1-6}$ alkoxy, wherein said $C_{1-6}$ alkyl or $C_{1-6}$ alkoxy may independently be further substituted with a halogen, $C_{1-6}$ alkyl or an oxo group;

$X_1$ and $X_2$ are N;

Y is selected from —$SO_2$— and —CO—;

Z is —CONHOH, Y is —CO— and Q is selected from —C(R6)(R7)-, —C(R6)(R7)-CH$_2$—, —N(R6)-, and —N(R6)-CH$_2$— wherein R6 is as defined above, and solely in relation to Q as here defined, R6 may also represent up to $C_{10}$ aryl and up to $C_9$ heteroaryl, and R7 is H, $C_{1-6}$ alkyl, or together with R6 forms a carbocyclic or heterocyclic spiro 5, 6 or 7 membered ring, the latter containing at least one heteroatom selected from N, O, and S;

Z is —CONHOH, Y is —$SO_2$— and Q is selected from —C(R6)(R7)-, and —C(R6)(R7)-CH$_2$—;

or Z is —N(OH)CHO and Q is selected from —CH(R6)-, —CH(R6)-CH$_2$—, and —N(R6)-CH$_2$—;

R1 is H, or $C_{1-6}$ alkyl;

Z is selected from —COOH, —CONHOH, —N(OH)CHO and N(OH)COR wherein R is $C_{1-6}$ alkyl, up to $C_{10}$ aryl and up to $C_9$ aralkyl And R2 is a ring having 5–7 ring atoms and comprising one or two ring heteroatoms independently selected from oxygen, nitrogen and sulphur, the ring being optionally substituted by (i) Y—R9 wherein R9 is $C_{1-6}$ alkyl, up to $C_{10}$ aryl, up to $C_{12}$ aralkyl or up to $C_{12}$ heteroaryl(hetero)alkyl, or (ii) Y-T-R9 wherein Y and R9 are as previously defined and T is oxygen or N—R8 wherein R8 is hydrogen or $C_{1-6}$ alkyl the heteroatom(s) being independently selected from oxygen, nitrogen and sulphur, R9 and R8 independently being optionally substituted by one or two groups selected from halogen, $NO_2$, CN, $CF_3$, $C_{1-6}$ alkyl, —S—$C_{1-6}$ alkyl, —SO—$C_{1-6}$ alkyl, —$SO_2$—$C_{1-6}$ alkyl and $C_{1-6}$ alkoxy;

or a pharmaceutically-acceptable salt or in vivo hydrolysable precursor thereof.

2. A compound as claimed in claim 1 and wherein:

R3 is hydrogen, halogen, $NO_2$, $CF_3$, $C_{1-4}$ alkyl, and $C_{1-4}$ alkoxy;

n is 1 or 2;

P is —(CH$_2$)n- wherein n is 0 or 1;

one or both of X2 and X1=N;

Y is —$SO_2$— or —CO—;

Q is —CH(R6)-, —CH(R6)-CH$_2$—, —N(R6)-, and —N(R6)-CH$_2$— wherein R6 is hydrogen or $C_{1-6}$ alkyl; when Q=—N(R6)- or —N(R6)-CH$_2$— then Y may also be —CS—, also Q may be linked to R1 or R2 to form a 5–7 alkyl or heteroalkyl ring;

R1=hydrogen, or $C_{1-4}$ alkyl;

Z=—CONHOH— or —N(OH)CHO and R2 is a ring having 5–7 ring atoms and comprising one or two ring heteroatoms independently selected from oxygen, nitrogen and sulphur, the ring being optionally substituted by (i) Y—R9 wherein R9 is $C_{1-6}$ alkyl, up to $C_{10}$ aryl, up to $C_{12}$ aralkyl or up to $C_{12}$ heteroaryl(hetero)alkyl, or (ii) Y-T-R9 wherein Y and R9 are as stated in claim 1 and T is oxygen or N—R8 wherein R8 is hydrogen or $C_{1-6}$ alkyl, the heteroatom(s) being independently selected from oxygen, nitrogen and sulphur; R9 and R8 independently being optionally substituted by one or two groups selected from halogen. $NO_2$, CN, $CF_3$, $C_{1-6}$ alkyl, —S—$C_{1-6}$ alkyl, —SO—$C_{1-6}$ alkyl, —$SO_2$—$C_{1-6}$ alkyl and $C_{1-6}$ alkoxy;

or a pharmaceutically-acceptable salt or in vivo hydrolysable precursor thereof.

3. A compound as claimed in claim 1 and wherein:

R3 is hydrogen, chlorine, flourine, $NO_2$, $CF_3$, methyl, ethyl, methoxy, ethoxy;

ring B is phenyl, biphenyl, napthyl, pyridyl pyrimidinyl, pyrazinyl and pyridazinyl;

P is a direct bond;

both X2 and X1 are N;

Y is —$SO_2$—;

Q is —CH$_2$—;

R2 is a ring having 5–7 ring atoms and comprising one or two ring heteroatoms independently selected from oxygen, nitrogen and sulphur, the ring being optionally substituted by (i) Y—R9 wherein is as stated in claim 1 and R9 is $C_{1-6}$ alkyl or alkylamino, up to $C_{10}$ aryl or arylamino, up to $C_{12}$ aralkyl or aralkylamino, up to $C_{12}$ heteroaryl(hetero)alkyl, R9 independently being optionally substituted by one or two groups selected from halogen, $NO_2$, CN, $CF_3$, $C_{1-6}$ alkyl, —S—$C_{1-6}$ alkyl, —SO—$C_{1-6}$ alkyl, —$SO_2$—$C_{1-6}$ alkyl and $C_{1-6}$ alkoxy;

R1 is hydrogen

Z is —N(OH)CHO;

or a pharmaceutically-acceptable salt or in vivo hydrolysable precursor thereof.

4. A compound as claimed in claim 1 and wherein:

R3 is methoxy, fluorine or 4-fluoro;

ring A is unsubstituted;

R2 is optionally substituted 3-piperidinyl, 4-piperidinyl or N-substituted 4-piperidinyl, or wherein the substituents are stated in claim 3;

or a pharmaceutically-acceptable salt or in vivo hydrolysable precursor thereof.

5. A compound as claimed in claim 1 and wherein R2 is 3- or 4-piperidinyl, optionally N-substituted by Y—R9 wherein Y is as stated in claim 1 and R9 is $C_{1-4}$ alkyl or alkylamino, $C_6$ aryl or arylamino, up to $C_{10}$ aralkyl or aralkylamino or up to $C_{10}$ heteroaryl(hetero)alkyl, R9 independently being optionally substituted by one or two groups selected from halogen, $CF_3$, and $C_{1-4}$ alkyl;

or a pharmaceutically-acceptable salt or in vivo hydrolysable precursor thereof.

6. A pharmaceutical composition which comprises a compound of the formula (I) as claimed in claim 1 or a pharmaceutically acceptable salt or an in vivo hydrolysable ester and a pharmaceutically acceptable carrier.

* * * * *